US011522989B2

(12) United States Patent
Crosby et al.

(10) Patent No.: US 11,522,989 B2
(45) Date of Patent: Dec. 6, 2022

(54) UV-C SANITIZING PHONE CASE AND MOBILE PHONE

(71) Applicant: Crosby Innovations, LLC, Detroit, MI (US)

(72) Inventors: Douglas A Crosby, Port Huron, MI (US); Kevin Scott Beedon, Mountain View, CA (US)

(73) Assignee: Crosby Innovations, LLC, Detroit, MI (US)

( * ) Notice: Subject to any disclaimer, the term of this patent is extended or adjusted under 35 U.S.C. 154(b) by 0 days.

(21) Appl. No.: 17/339,515

(22) Filed: Jun. 4, 2021

(65) Prior Publication Data

US 2021/0385317 A1 Dec. 9, 2021

Related U.S. Application Data

(60) Provisional application No. 63/034,967, filed on Jun. 4, 2020.

(51) Int. Cl.
*H04M 1/17* (2006.01)
*A61L 2/10* (2006.01)
*A61L 2/26* (2006.01)
*A61N 5/06* (2006.01)

(52) U.S. Cl.
CPC ............... *H04M 1/17* (2013.01); *A61L 2/10* (2013.01); *A61L 2/26* (2013.01); *A61N 5/0624* (2013.01); *A61L 2202/11* (2013.01); *A61L 2202/14* (2013.01); *A61L 2202/16* (2013.01); *A61L 2202/26* (2013.01); *A61N 2005/0651* (2013.01); *A61N 2005/0661* (2013.01)

(58) Field of Classification Search
CPC ................ H04M 1/17; A61L 2/10; A61L 2/26
See application file for complete search history.

(56) References Cited

U.S. PATENT DOCUMENTS

| 2013/0063922 | A1* | 3/2013 | La Porte | A61L 2/10 250/455.11 |
| 2016/0036952 | A1* | 2/2016 | Kim | H04B 1/3888 455/575.8 |
| 2017/0304472 | A1* | 10/2017 | Neister | A61L 2/0011 |
| 2018/0161594 | A1* | 6/2018 | Yehezkel | A61L 2/10 |
| 2018/0177908 | A1* | 6/2018 | Ochi | A61L 9/20 |
| 2019/0075900 | A1* | 3/2019 | Hynecek | A45C 11/00 |
| 2019/0167827 | A1* | 6/2019 | Gaska | A61L 2/24 |
| 2020/0316238 | A1* | 10/2020 | Zhang | A61L 2/24 |

* cited by examiner

*Primary Examiner* — Kevin Joyner
(74) *Attorney, Agent, or Firm* — Loomis, Ewert, Parsley, Davis & Gotting, PC; Mikhail Murshak (57) ABSTRACT

A UV-C emitting phone case is provided that includes a main body defining a receiving cavity and a perimeter configured to receive and hold a mobile phone, surround a perimeter and a back portion of the phone. The phone case includes at least one UV-C light emitting diode (LED) positioned in the main body of the phone case and exposed on a back side of the phone case. It further includes a window for exposing the UV-C LED and optionally having a color metric to indicate if the light is being emitted, a power source built into the phone case and connected to the UV-C LED; an on/off switch coupled to the power source configured to activate and deactivate the UV-C LED; and an optional distance sensor to indicate a distance from a target surface to the UV-C LED.

17 Claims, 5 Drawing Sheets

UV-C SANITIZING PHONE CASE AND MOBILE PHONE

CROSS REFERENCE TO RELATED APPLICATION

This application claims priority to U.S. Provisional Application 63/034,967 filed Jun. 4, 2020 which is incorporated herein by reference in its entirety.

FIELD

The present disclosure relates generally to an apparatus, system, and method for sanitizing using UV-C light applied to surfaces and to human skin.

BACKGROUND

The statements in this section merely provide background information related to the present disclosure and may not constitute prior art.

There are various methods and devices that are capable of being utilized to remove germs, bacteria and/or other microorganisms. For example, it is known to use liquids, such as alcohols, acids, and bases, to clean hands.

It is also known to use radiation, such as light, to clean objects by using the light to destroy microorganisms on the surface of the objects. For example, ultra-violet ("UV") light with a wavelength between approximately 100 to 280 nanometers (also referred to as "UV-C light") can be used as a germicide by destroying the DNA in microorganisms and thereby killing the microorganisms. However, many of the devices that use UV-C light are large and bulky, making such devices difficult to move around and use with the ease of other germicide devices, like the liquid germicide discussed above. Moreover, some of the smaller UV-C light bactericidal devices are portable but require a wired connection to an electrical outlet or are too large to carry around inconspicuously. There is a need for better hygiene through improved germicide devices and methods without the need for liquids.

SUMMARY

The present disclosure provides for an ultra-violet (UV) light sanitizing phone case or phone having one or more light emitting diodes (LEDs). UV light can be broken down into different ranges based on the wavelengths of the UV light. UV-A light wavelengths range from 315 nm to 400 nm. UV-B light wavelengths range from 280 nm to 315 nm. UV-C light wavelengths range from 100 nm to 280 nm. A desired range for human skin applications is 200 nm to 240 nm, including 220 nm to 230 nm. UV-C light has the natural property of killing germs including fungi and protozoans and including killing bacteria and disabling viruses by destroying the DNA or RNA found in the bacteria or virus. UV light may be harmful to human skin and human eyes in the form of cancer and permanent eye damage if used improperly. However, when used properly, UV-C light can safely kill and disable germs on human skin without causing any damage or irritation, particularly at the desired wavelength ranges. Still further, when used properly, UV-C light can safely kill and disable germs on gloves and other surfaces without causing any damage or irritation, particularly at the desired wavelength ranges. In yet another example, the UV-C light can safely kill viruses like the coronavirus SARS-CoV-2 responsible for causing Covid-19 off hands and desired surfaces and thus enhance surface contact safety and help eradicate Covid-19.

UV-C light can be effective in sanitizing and disinfecting surfaces and materials such as personal protective equipment (PPE) like gloves, masks, and gowns. This can be especially useful during times of equipment shortages, like a pandemic, by providing a process to reuse single-use or disposable equipment. In an example, UV-C light at a wavelength of 222 nm has been shown to effectively kill over 95% of the influenza virus at a low dose of 2 mJ/cm$^2$ while not even penetrating an outer dead-cell layer of human skin or a tear-layer on a human eye. Using an arrangement of lower power consumption LED's, UV-C light can be emitted at a wavelength suitable to kill, destroy, or reduce growth of microorganisms/germs within the area proximate to the housing, which can serve to sanitize and disinfect human skin or a surface of PPE exposed to the UV light for a suitable amount of time.

In a further example, the wavelength of UV-C light emitted from the LEDs is between about 100 and 280 nm, or 200 and 265 nm, or 220 and 230 nm. Exposing the UV-C light onto a close surface or human skin, like hands and other parts of the body, can actively sanitize and kill germs present on the surface or skin. This can help prevent the spread of germs, viruses, and bacteria and contribute significantly to prevent pandemics and stop the spread of diseases, particularly in large crowded areas like concerts, airports, churches, schools, sporting events, and the like.

An example phone case is formed to partially enclose a circuit board and one or more LEDs that are integrated into the case for a mobile device like a mobile phone. In one example, each LED defines a width of about 3 mm to 5 mm and is configured to receive a current of about 20 mA and a power consumption of about 70 mW. In another example, the phone case is suitable to kill at least 99% of unwanted microorganisms such as bacteria and viruses within proximity of the case. The case can include a battery pack for power supply to the LEDs and activation buttons provided on the case. In another example, the LEDs for emitting UV-C light are incorporated directly into a mobile phone with proper battery charging and activation buttons provided.

In an example, the phone case includes a plurality of LEDs. Each LED is configured to emit UV-C light and individually connected to a power source. In an example, the power source is a simple battery like an off-the-shelf alkaline or Lithium-ion battery and incorporated into the device. The apparatus can further include an optional on/off switch or button positioned along the outside of the case and coupled to the power source. The switch or button is operable for causing the LEDs to turn on and off upon actuation thus activating the emitting of the UV-C light.

The case can be fabricated from a plastic with various openings to accommodate camera and plug features of a corresponding phone. The case can include indicator lights to convey that the UV-C light is on and the charge state of the battery. In an example, the indicator lights are positioned at a base or bottom portion of the case and the LED or LEDs emitting the UV-C light are positioned at a top portion of the case. Internal connections from the battery to the light are integrated and unexposed within the case. Upon activation of the LEDs, the UV-C light can emit onto a user's hands, gloves, or a desired surface or object to sterilize and sanitize. The emission of light should be at a power sufficient to sanitize and disinfect a surface (i.e., hands/skin of a user, gloves, or desired surface) when placed near the lights for a predetermined period of time. The UV-C light can be emitted at a wavelength suitable to kill, destroy, or reduce growth of microorganisms/germs within the area proximate to the case. The UV-C light emitted from the LEDs efficiently kills, destroys, or reduces the growth of microorganisms, viruses, and other germs on the user's hands.

Further areas of applicability will become apparent from the description provided herein. It should be understood that the description and specific examples are intended for purposes of illustration only and are not intended to limit the scope of the present disclosure.

DRAWINGS

In order that the disclosure may be well understood, there will now be described various forms thereof, given by way of example, reference being made to the accompanying drawings in which.

The drawings described herein are for illustration purposes only and are not intended to limit the scope of the present disclosure in any way.

DETAILED DESCRIPTION

The following description is merely exemplary in nature and is not intended to limit the present disclosure, application, or uses. It should be understood that throughout the drawings, corresponding reference numerals indicate like or corresponding parts and features.

Handheld and standalone UV-C devices and applications were previously disclosed in co-owned applications: U.S. patent application Ser. No. 16/853,081 filed May 11, 2020 which claims priority to Provisional Application No. 63/000,186 filed Mar. 26, 2020 and is a continuation-in-part of U.S. patent application Ser. No. 15/975,262 filed on May 9, 2018, which claimed priority to U.S. Provisional Application No. 62/503,912 filed May 9, 2017, the subject matter of which are incorporated by reference in their entirety.

The present disclosure provides for an improved handheld sanitization and/or sterilization device built into a phone case for holding a mobile phone or mobile device. In another example, the present disclosure provides for an improved handheld sanitization and/or sterilization device built directly into a mobile phone or mobile device.

The phone case is capable of improved sanitizing and sterilizing of an area proximate the device such as human skin, a hand or hands of a user, gloves, or a desired surface. Ultraviolet (UV) light, specifically UV-C light, is an effective sterilization agent because UV light breaks down living organisms, rendering them harmless. The device according to the present disclosure includes at least one and sometimes a plurality of UV emitting lights positioned within a case. The UV light emitted from the case is operable to destroy and disable germs, bacteria, and/or viruses. The UV light referred to in this disclosure is short-wavelength ultraviolet "UV-C", which functions as a germicide and is less harmful than other wavelengths of UV light such as UV-A or UV-B. Accordingly, reference to "UV light" should be considered UV-C light for purposes of this disclosure. The UV-C light can safely kill viruses like the coronavirus SARS-CoV-2 responsible for causing Covid-19 off hands and desired surfaces and thus enhance surface contact safety and help eradicate Covid-19.

Figure 1:
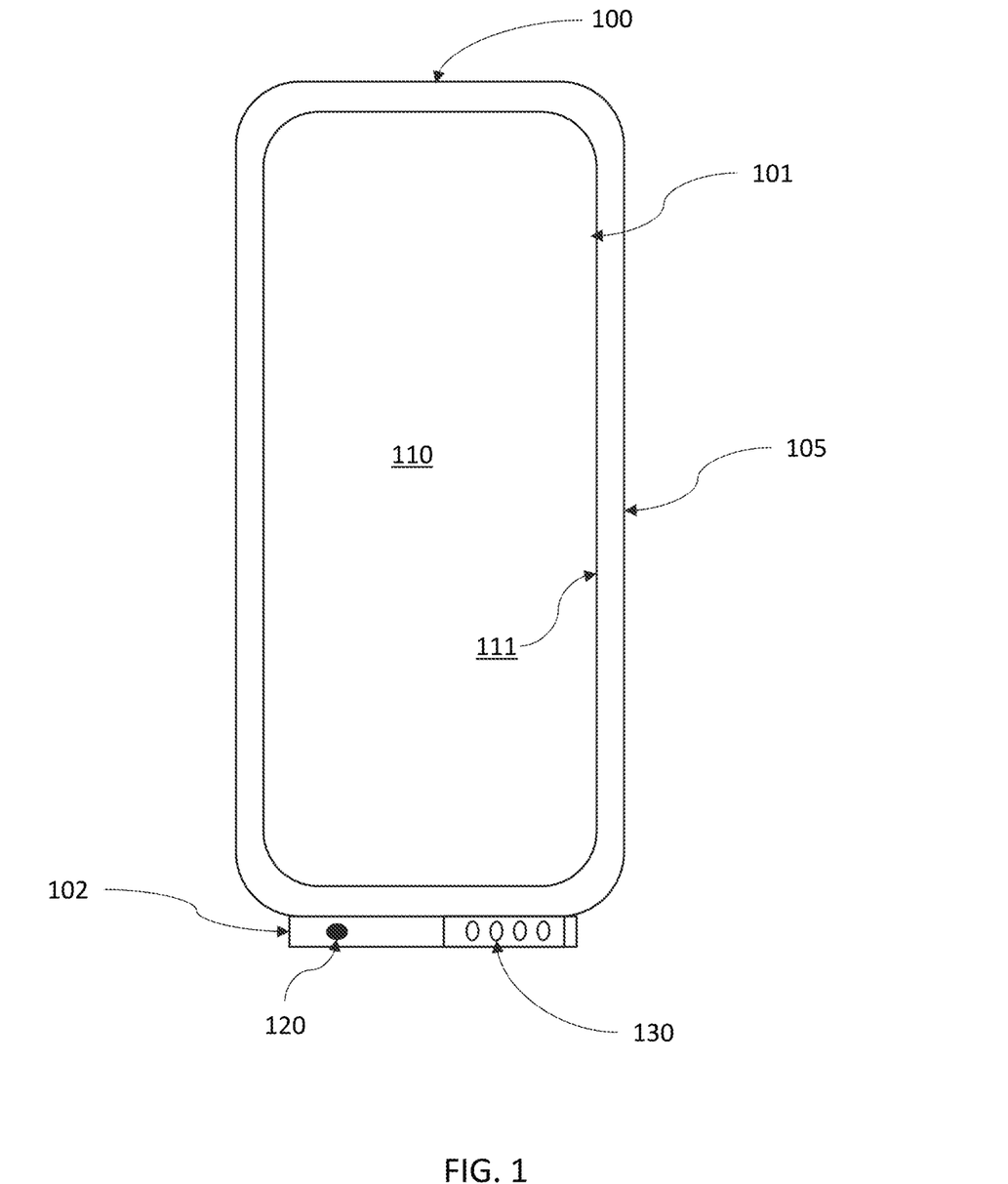
FIG. 1 illustrates a schematic front face view of an example phone case according to the present disclosure showing the indicator lights positioned at a bottom section of the case.
Figure 2A:
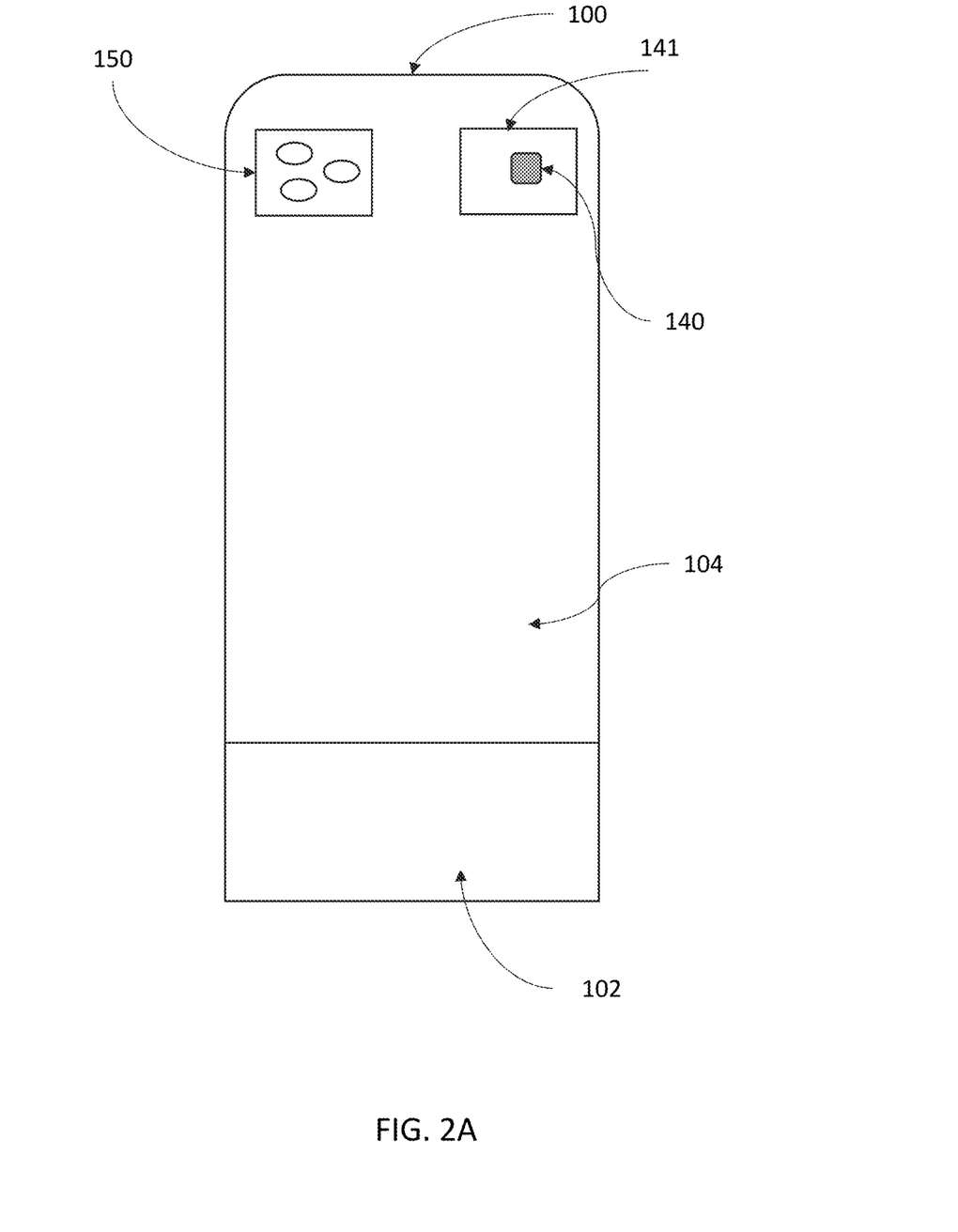
FIG. 2A illustrates a schematic back side view of the phone case of FIG. 1 showing the UV-C light window and battery section built into the case.
Figure 2B:
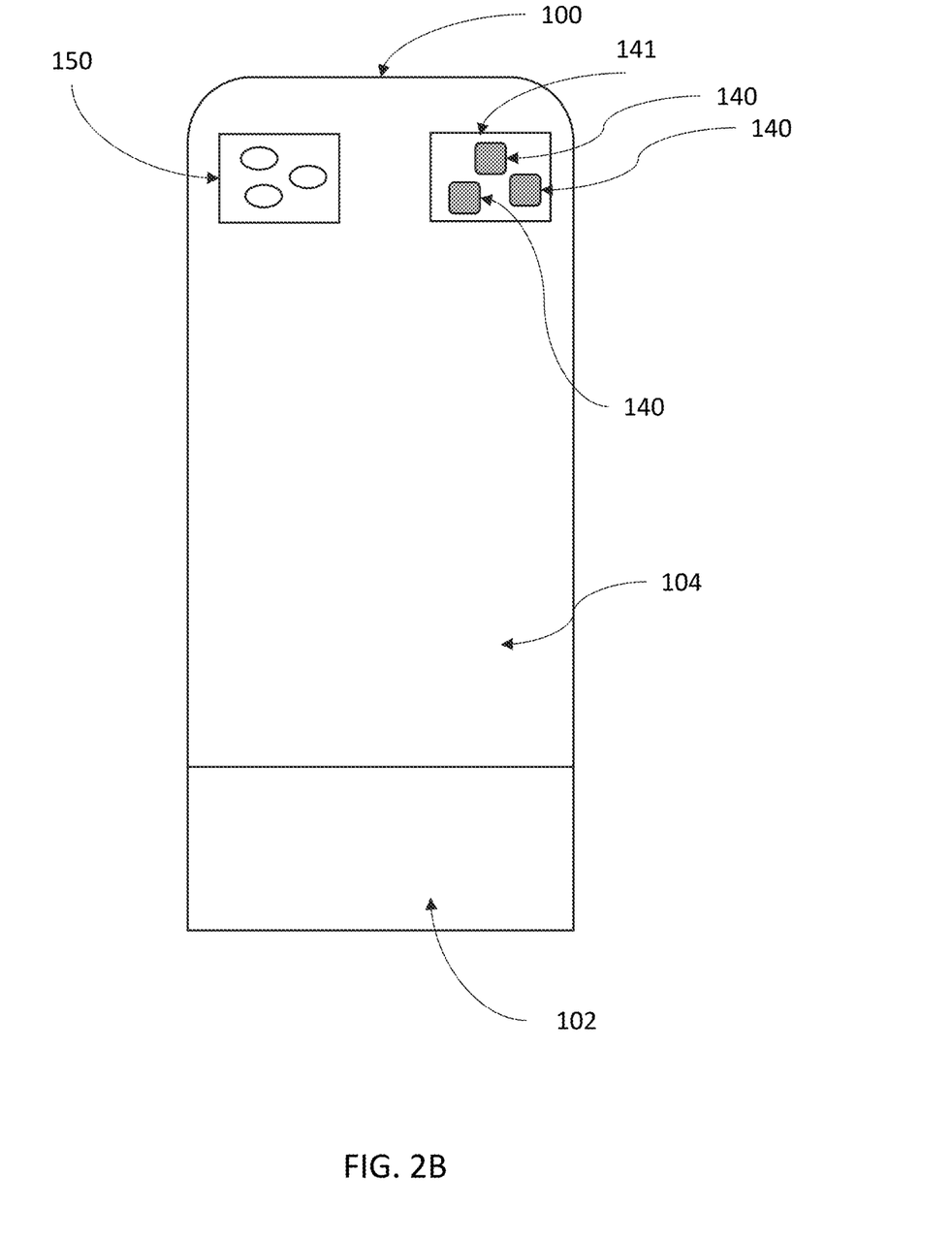
FIG. 2B illustrates a schematic back side view of the phone case of FIG. 1 having a plurality of UV-C LEDs showing the UV-C light window and battery section built into the case.

With reference now to the drawings, FIGS. 1 to 4B illustrate example schematic embodiments of a phone case having at least one integrated UV-C light emitting diode ("LED") integrated into the case, connected to a battery feature to provide power, and one or more indicator lights to indicate certain features such as if the UV-C light is on or off and the charge status of the battery. FIGS. 1-2 illustrate a front and rear view, respectively, of an example phone case 100 having a UV-C LED integrated into the case. Phone case 100 is sized and shaped to receive a mobile device or mobile phone having a touch screen 110. The phone can be of varying sizes and shapes depending on the brand and model of the phone. The dimensions of the case can be adjusted appropriately to accommodate the variety of phones available.

In this example, case 100 includes a receiving cavity 101 and an outer rim 105 that receives the phone and surrounds a perimeter of the phone 111 while exposing the phone screen 110. The receiving cavity 101 defines a depth sufficient to receive a body of the phone and surround and hold the phone with the front touch screen 110 exposed. At or near a bottom portion of case 100, a portion of a battery housing 102 is shown with UV-C activation light 120 to provide a visual indication of whether the UV-C light is turned on or off. Further, a battery indicator light or lights 130 can be provided to indicate a charge status of the battery.

As shown in FIGS. 2A and 2B, the phone case 100 encloses and extends across an entire back side of the phone, forming a main body 104. The UV-C LED 140 is integrated into the main body 104 and configured to emit light out and away from the case 100. FIG. 2B shows an example with a plurality of LEDs 140. In this example, the UV-C LED 140 or LEDs 140 are connected to a battery that is built directly into the case 100 at battery housing section 102. In this example, the LED(s) 140 are provided at a top section of the backside of case 100 and the battery housing section 102 is positioned at a bottom section of the backside of case 100. The connection wiring 107 between the UV-C LED 140 and the battery housing section 102 is integrated directly into the case 100. In this example, case 100 includes an opening 150 to accommodate a camera area for a typical mobile phone having one or more cameras.

In one example, the battery incorporated into the battery housing section 102 is operable to connect to the phone through a charging port provided on most phones to pull a charge from the phone when available or vice versa so that the UV-C LED is charged or powered by the mobile device itself. In yet another example, the phone is equipped with a downloadable application (an "app.") that functions to operate and communicate the status of the UV-C LED emission. In such an example, the status of the UV-C phone cases and corresponding data can be communicated through a wireless communication module or directly through the charge port. A visual display of the status of the UV-C activation, including time of emission, a proxy for what percentage of germs that are killed during use or an entertaining graphic, and other features, can be provided on the phone screen 110 during use and activation of the app. The battery (not shown) in battery housing 102 can be rechargeable and includes a charging port. In another example, the case connects to the phone and charges directly from the phone's battery.

Figure 3:
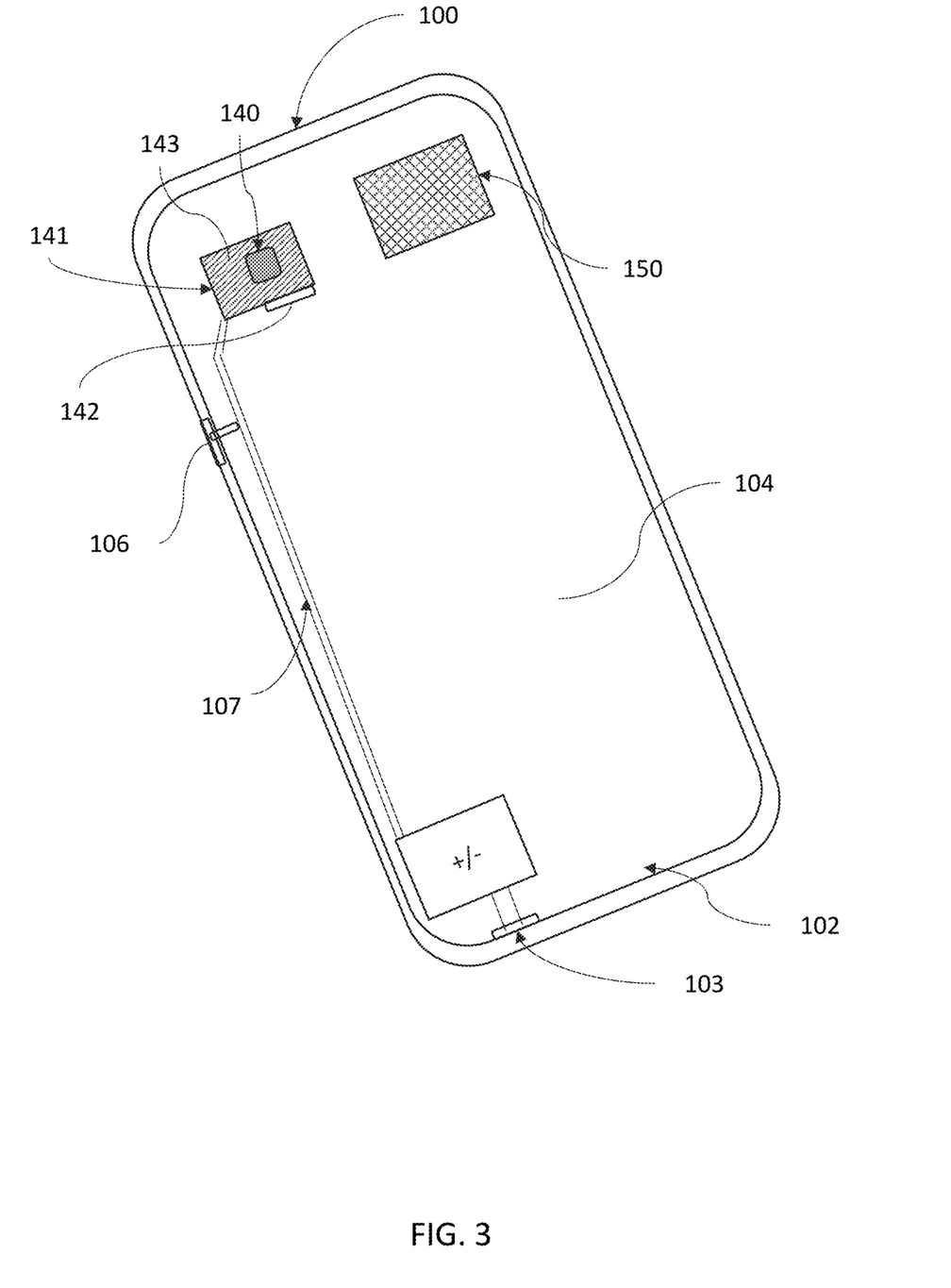
FIG. 3 illustrates a schematic view of an alternative example of a backside view of a phone case with a UV-C LED integrated therein with an indicator window showing the internal components.
Figure 4A:
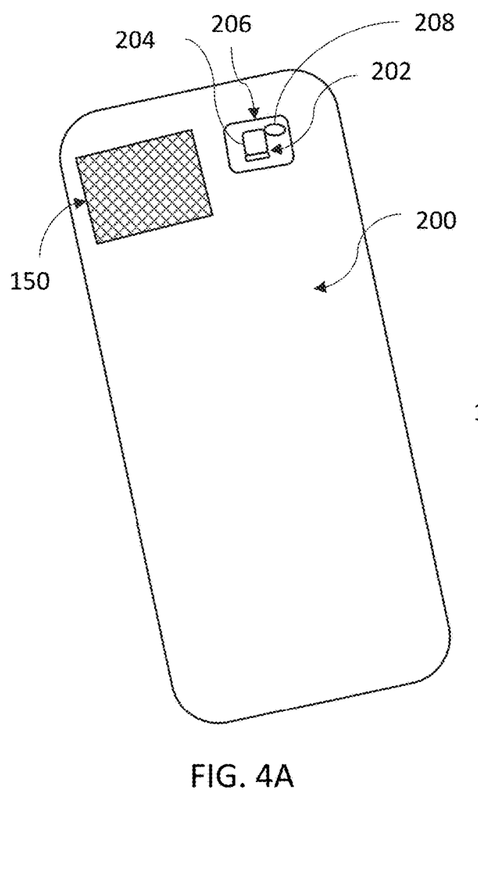
FIG. 4A illustrates a schematic view of an example cell phone with a built in UV-C LED for use in sanitizing.
Figure 4B:
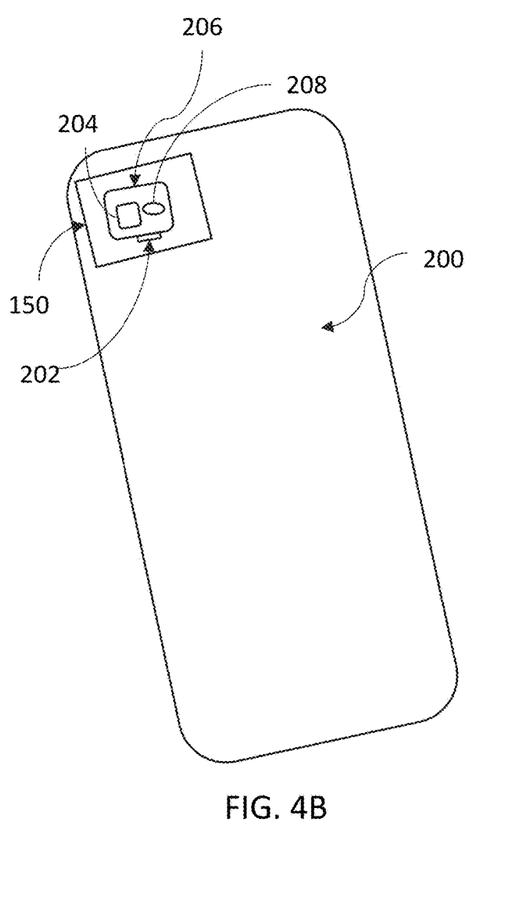
FIG. 4B illustrates a schematic view of an example cell phone with a built in UV-C LED in a different position as compared to FIG. 4A for use in sanitizing.

In the example of FIG. 3-4, an example phone case 100 is shown is shown in a transparent view to show internal components. In this example, the phone case 100 includes a hole or opening 141 for UV-C LED 140 covered with either a flat or convex window 143. A lens (not shown) can also be used to focus the emission of UV-C light. In this example, window 141 can be a fluorescent or other color metric that changes color when the UV-C light is emitting to provide further indication that the UV-C light is active and where the UV-C light is being directed. This feature provides for added safety and information to a user. In a further example, window 143 is made from quartz. Window 143 should be configured to allow for sufficient UV-C light emission to achieve a desired sanitization. In a further example, a fluorescent light, like a fluorescent LED, can be used for safety in order to indicate when and where the UV-C light (which is invisible) is active. Thus, the fluorescent light is activated when the UV-C LED 140 is activated.

In a further example, a filter (not shown), like a lens, is provided that is configured to filter far UV-C light. In a further example, a crystal or other conversion material is provided like a prism. The filtering feature can limit undesired emission or limit the bandwidth intensity of the emission like. In another example, the UV-C light can be utilized to kill undesired particles in the air as an air sanitizer to specially kill the germs, mold spores, mildew, bacteria and even viruses.

In this example, a battery charge hole 103 is provided at a bottom section that is connected to a battery such as an off-the-shelf alkaline or lithium-ion battery. In this example, the battery is provided in housing section 102 and is flush with the case body 104. An on/off relay switch 106 is positioned on a side of the case 100 that connects to wiring 107 to activate or turn off the UV-C LED. In an example, the relay switch 106 can be a timer-color indicator to indicate whether it is on or off.

The emission of UV-C light should be within a safe wavelength range as previously discussed to be safe to human skin and nearby surfaces. Accordingly, using a phone case 100, a user can safely disinfect his or her hands, gloves, or other surfaces. In a further example, the body 104 of case 100 can be made of plastic and include at least some copper or silver that is naturally antimicrobial. In a further example, positioned just below the hole 141 for UV-C LED 140 is an optional distance tracker sensor 142 that tracks the distance away from a target, like skin of a person, gloves, or a desired surface. An appropriate distance can be from a few centimeters up to a several inches. This can be communicated through a corresponding app, or through a light or other indicator.

FIGS. 4A-4B provide for different examples of a mobile device 200 with one or more UV-C LEDs that are built directly into the mobile device itself. In these examples, the mobile device 200 is shown from a backside view to show exposure of the UV-C LED(s) 204. Typical mobile devices 200 include one or more camera features indicated by box 150. The mobile device 200 includes an optional distance tracker 202 and a UV-C LED 204 positioned within a window 206. In this example, the individual LED 204 or LEDs are mounted directly and integrated with the phone 200 itself. The UV-C LED 204 can be activated by the internal phone software or controlled by a downloadable app. The emission of UV-C light should be within a safe wavelength range as previously discussed to be safe to emit on human skin and nearby surfaces. Fluorescent light 208, like a fluorescent LED, can be used for safety in order to indicate when and where the UV-C light (which is invisible) is active. Thus, the fluorescent light 208 is activated when the UV-C LED 204 is activated. An on/off safety feature can further be provided and built into the phone's software. The phone can track the quantity and quality of use or activated by selecting, through the app, a desired sanitization like hands, gloves, or desired surface. In another example, the UV-C LED 204 is positioned at various positions as shown that are different like FIG. 4A shows the LED on an upper right portion and FIG. 4B shows the LED on an upper left portion.

An on/off switch 106 of the phone cases from FIGS. 1-3 can be provided to allow activation of the one or more LEDs 140. Each LED 140 is adapted to emit UV light sufficient to sanitize or sterilize a surface within its proximity or a measured emission zone. The range for sterilization depends on the emission power of each LED. In this example, a Lithium (Li+) ion battery or equivalent is used, however, disposable and/or rechargeable batteries are within the scope of this disclosure. In this example, each LED can be adapted to receive a current of about 20 mA and a power consumption of about 70 mW while delivering UV light having a wavelength in the range of between about 100 nm and 280 nm, 200 and 250 nm, 220 and 230 nm. In a further example, each LED is sufficient to emit UV-C light at a wavelength of about 232 or 233 nm.

The present disclosure provides for a method of sterilizing/sanitizing hands of a user by providing a phone case or a phone from FIGS. 1-4 having one or more UV-C emitting LEDs and activating the LEDs to emit the UV-C light out from the phone or the phone case to expose a user's skin or surface to the UV-C light. In use, for example, a user may turn on the UV-C LED by pushing an on/off switch and thus activating the LED or LEDs to emit UV-C light onto one or more hands, skin, or surface. Holding the LED light for several seconds to a minute or more allows for desired sanitizing or sterilizing without the need for undesired liquids or alcohols. In this example, the UV light technology is sufficient to kill or reduce viruses, and any present parasitic DNA. Thus, undesired and harmful germs are cleaned from the hands of a user.

The LED or LEDs are configured to emit UV-C light, which has ranges in wavelengths from 100 nm to 280 nm. UV-C light has the natural property of killing germs, including killing bacteria and disabling viruses. UV light in many forms is harmful to human skin and human eyes, however, when used properly, UV-C light can safely kill and disable germs on human skin without causing any damage or irritation. Specially, UV-C light at a wavelength of 222 nm has been shown to effectively kill bacteria and other microorganisms while not even penetrating the outer layer of the human skin or the human eye. In an example, the LED or LEDs are configured to emit UV-C light at a wavelength of about 222 nm. Moreover, UV-C light can be effective in sanitizing and disinfecting surfaces and materials such as personal protective equipment (PPE) like gloves, masks, and gowns. This can be especially useful during times of equipment shortages, like a pandemic, by providing a process to reuse single-use or disposable equipment.

LEDs have many advantages over other light sources, including lower energy consumption, longer lifetime, improved physical robustness, smaller size, and faster switching. In an example, a user can leave the hands under the UV-C light for at least 5 seconds to 60 seconds and more specifically for at least 6 seconds to 30 seconds and yet further for 6 seconds to 10 seconds to achieve a desired sterilization. It is helpful if the user manually moves the light around the surface of the skin for intended sterilization during exposure. The phone case can be equipped with indicia like a timer or a light indicator to convey to the user that the sufficient exposure time has been met. This can be done in a variety of ways, including multiple "percent clean" indicator such as 10% clean, 50% clean, 70% clean, and complete. Moreover, the apparatus can automatically turn off when the preset time for emission time has surpassed. The amount of time left under the UV-C light can also be proportionate to the targeted bacteria, virus, or other microorganisms.

The present disclosure further provides for a method of sterilizing and sanitizing PPE such as disposable protective gloves, reusable protective gloves, masks, and gowns. In this example, the phone case can be used to clean undesired and harmful germs on protective gloves. Protective gloves protect the user from harmful germs, bacteria, and viruses from the environment. However, once the germs, bacteria, or viruses attach to the gloves, the gloves are compromised and can lead to the user self-infecting or infecting others. Typically, the user would need to either dispose of or wash the compromised gloves to protect and avoid future infections or contaminations. In this example, the user can position the hands with the protective gloves under the phone or phone case whereby the LED emitting UV-C light exposes a user's gloves to the UV-C light. The UV-C light is emitted at a wavelength that is sufficient to kill or reduce viruses, and any present parasitic DNA. Thus, undesired and harmful germs are cleaned from the protective gloves of a user. In a further example, this phone case or phone with UV-C LED is configured to kill coronavirus. This method of sterilizing/sanitizing protective gloves reduces waste and minimizes costs by allowing for multiple uses of disposable protective gloves and reduces the washing of compromised, reusable protective gloves.

The foregoing description of various forms of the invention has been presented for purposes of illustration and description. It is not intended to be exhaustive or to limit the invention to the precise forms disclosed. Numerous modifications or variations are possible in light of the above teachings. The forms discussed were chosen and described to provide the best illustration of the principles of the invention and its practical application to thereby enable one of ordinary skill in the art to utilize the invention in various forms and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A UV-C emitting mobile device case comprising:
   (a) a main body defining a receiving cavity and a perimeter configured to receive and hold a mobile device and surround a perimeter and a back portion of the mobile device configured to allow access to and exposure of a display screen of the mobile device;
   (b) at least one UV-C light emitting diode (LED) configured to emit UV-C light from the LED at a wavelength between 200 and 250 nm and positioned in the main body of the mobile device case and exposed on a back side of the main body through a window; and
   (c) a power source built into the mobile device case and connected to the UV-C LED and coupled to an on/off switch configured to activate and deactivate the UV-C LED, wherein the power source is connected to the mobile device and configured to draw power directly from the mobile device; and
   (d) a distance sensor configured to indicate a distance from a target surface to the UV-C LED;
   wherein the UV-C light emitted from the UV-C LED is configured to kill germs and viruses, and
   wherein the UV-C light is coupled to a mobile application hosted on the mobile device configured to activate the at least one UV-C LED, control the wavelength of emission, and provide a status of activation.

2. The mobile device of claim 1, wherein the window includes a color metric to indicate if the UV-C light is being emitted and the color metric is fluorescent configured to emit a visible color when the UV-C LED is activated and the window is a transparent plastic or glass and the visible color is activated by the UV-C light emission.

3. The mobile device case of claim 1, further comprising a filtering lens configured to limit the bandwidth of the UV-C light emission.

4. The mobile device case of claim 1 wherein the UV-C LED is configured to emit light at a wavelength in a range from 220 to 230 nm.

5. The mobile device case of claim 1 wherein the UV-C LED is configured to emit light at a wavelength of 222 nm.

6. The mobile device case of claim 1 further comprising wa plurality of UV-C LEDs arranged on a circuit board connected to the power source and spaced apart relative to each other to emit UV-C light to cover a broader area as compared to a single UV-C LED.

7. The mobile device case of claim 1 wherein the window defines a convex shape.

8. The mobile device case of claim 1 wherein the window includes quartz glass.

9. The mobile device case of claim 1, wherein a front side of the phone case includes an LED indicator and a battery charge indicator.

10. The mobile device case of claim 9, wherein the LED indicator and the battery charge indicator include indicator lights positioned at a bottom portion of the phone case.

11. The mobile device case of claim 1, further comprising at least one fluorescent LED light configured to activate and emit a visible color to indicate if the UV-C light is being emitted.

12. The mobile device case of claim 1, wherein the UV-C light emitted from the LED is configured to safely disinfect skin of a user.

13. The mobile device case of claim 1, wherein the LED defines a width of about 3 mm to 5 mm and configured to receive a current of about 20 mA and a power consumption of about 70 mW.

14. The mobile device case of claim 1, wherein the UV-C emission is configured to kill at least 99% of unwanted germs or microorganisms within a preset exposure area present on a user's hands, skin, or gloves that come in contact with the emitted UV-C light.

15. The mobile device case of claim 1, wherein the UV-C emission is configured to kill viruses including SARS-CoV-2 to assist with prevention of Covid-19.

16. The mobile device case of claim 1, wherein the main body is fabricated from a material that includes copper or silver oxide operable to impart natural antimicrobial characteristics.

17. A UV-C emitting mobile device case comprising:
(a) a main body defining a receiving cavity and a perimeter configured to receive and hold a mobile device and surround a perimeter and a back portion of the mobile device configured to allow access to and exposure of a display screen of the mobile device;
(b) at least one UV-C light emitting diode (LED) configured to emit UV-C light from the LED at a wavelength between 200 and 250 nm and positioned in the main body of the mobile device case and exposed on a back side of the main body through a window; and
(c) a power source built into the mobile device case and connected to the UV-C LED and coupled to an on/off switch configured to activate and deactivate the UV-C LED, wherein the power source is connected to the mobile device and configured to draw power directly from the mobile device; and
(d) a distance sensor configured to indicate a distance from a target surface to the UV-C LED;
wherein the UV-C light emitted from the UV-C LED is sufficient to kill SARS-CoV-2 to assist with prevention of Covid-19, and
wherein the UV-C light is coupled to a mobile application hosted on the mobile device configured to activate the at least one UV-C LED, control the wavelength of emission, and provide a status of activation.

* * * * *